United States Patent [19]

Wilkins et al.

[11] Patent Number: 4,533,630

[45] Date of Patent: Aug. 6, 1985

[54] TOXINS AND ANTIBODIES OF *C. DIFFICILE*

[76] Inventors: Tracy D. Wilkins, 305 Neil St., Blacksburg, Va. 24060; David M. Lyerly, 37 Radford Village, Radford, Va. 24141

[21] Appl. No.: 417,379

[22] Filed: Sep. 13, 1982

[51] Int. Cl.$^3$ .................. G01N 33/54; C12Q 1/42; C07G 7/00
[52] U.S. Cl. .................. 435/7; 260/112 R; 436/543; 436/547; 435/21; 424/85; 424/87
[58] Field of Search .................. 424/85, 87, 88, 92; 260/112 R, 112 B; 436/535, 543, 544, 547; 435/7, 21

[56] References Cited

PUBLICATIONS

Libby et al., Abstrac., Annu. Meet. Am. Soc. Microbiol., 1981, B44, p. 22.
Libby et al., Infect. Immun., vol. 35, pp. 374–376, 1982.
American Type Culture Collection Catalog of Strains, 15th Edition, 1982, pp. 357, 377, 376, 526 and 527.
Taylor, N., et al., Infect. Immun., vol. 34, pp. 1036–1043, 1981.
Sullivan, N., et al., Infect. Immun., vol. 35, pp. 1032–1040, 1982.
Lyerly, D. et al., Infect. Immun., vol. 35, pp. 1147–1150, 1982.
Chemical Abstracts, vol. 98, Abst. No. 105333n, 1983.
Chemical Abstracts, vol. 95, Abst. No. 36781f, 1981.

*Primary Examiner*—Blondel Hazel
*Attorney, Agent, or Firm*—Elliot M. Olstein

[57] ABSTRACT

Mono-specific antibodies for each of toxin A and toxin B of *C. difficile* are produced and used in an assay for toxin A and toxin B, respectively. Purified toxin A of *C. difficile* is also produced.

38 Claims, No Drawings

TOXINS AND ANTIBODIES OF C. DIFFICILE

This invention relates to a C. difficile and more particularly to the production of antibodies to the toxins of C. difficile, purification of the toxins, and the use thereof in an assay for C. difficile toxins.

The anaerobic organism Clostridium difficile (C. difficile) is associated with antibiotic related pseudomembranous colitis and as a result, there have been tests developed to ascertain the presence of C. difficile antigen in specimens of human stool.

One such test involves culture of human feces, which requires specialized facilities and a long period of time. This test also detects strains of C. difficile that do not produce toxins, and thus gives false positive results.

Another test involves counter immunoelectrophosesis, however, this test, as currently used, is not sensitive enough to detect toxins and gives a lot of false positives.

A further test involves an enzyme immunoassay; however, such test, as currently used, does not differentiate between toxic and non-toxic strains, and as a result, the test may give misleading results.

The present invention is directed to antibodies for toxins of C. difficile, toxins of C. difficile, and an assay for toxigenic C. difficule.

In accordance with one aspect of the present invention, there is provided a mono-specific antibody for toxin A of C. difficile, and such mono-specific antibody supported on a solid support.

In accordance with another aspect of the present invention, there is provided a mono-specific antibody for toxin B of C. difficile, and such mono-specific antibody supported on a solid support.

In accordance with a further aspect of the present invention, there is provided pure toxin A of C. difficile, and such toxin on a solid support.

In accordance with yet another aspect of the present invention, there is provided an assay for toxin A of C. difficile which uses mono-specific antibody for toxin A.

In accordance with yet a further aspect of the invention, there is provided an assay for toxigenic C. difficile.

The term "mono-specific antibody for toxin A", as used herein, means an antibody which does not have any determinant sites for antigens of C. difficile other than toxin A.

The term "mono-specific antibody for toxin B", as used herein, means an antibody which does not have any determinant sites for antigens of C. difficile other than toxin B.

The term mono-specific antibody as used herein includes such antibody in a mono-clonal form.

It is to be understood that the mono-specific antibodies to toxin A and/or toxin B can be produced from an organism other than C. difficile, so long as the antibody does not have a determinant site for another antigen of C. difficile.

C. difficile antibody or antibody to C. difficile means antibody which is not mono-specific, and which therefore is comprised of a mixture of antibodies, which includes antibodies for toxins of C. difficile (antibody for toxin A and antibody for toxin B) and antibodies for non-toxins of C. difficile.

Antibody for toxigenic C. difficile or antibody specific for toxins of C. difficile means antibody which does not have determinant sites for antigens of C. difficile other than toxin A and toxin B (a mixture of antibody specific only for toxin A and antibody specific only for toxin B).

Toxin A is the C. difficile toxin that is generally referred to as the enterotoxin. Toxin A has a native molecular weight between 550,000 and 600,000, an isoelectric point of 5.5, contains no detectable carbohydrate or phosphorus and does not exhibit detectable protease activity. It is inactivated as pH 2.0 and is stable at a pH of 10.0. Toxin A is eluted from DEAE by a buffer containing 0.16M NaCl.

Toxin B is the C. difficle toxin which is generally referred to as the cytotoxin of C. difficile. Toxin B has a native molecular weight between 380,000 and 470,000, an isoelectric point of 3.8; contains no detectable phosphorus, but does contain very small amounts of carbohydrate (which may be a contaminant) and does not exhibit detectable protease activity. Toxin B is inactivated by pH's less than 2.0 and over 10.0. and is eluted from a DEAE column with a salt concentration of 0.4M.

It is to be understood, however, that although toxin A is referred to as the enterotoxin such toxin A also has cytotoxicity.

In accordance with one aspect of the invention, toxin A, which has been partially purified by separation from toxin B, and which still includes some nontoxigenic proteins is further purified to produce pure toxin A. In accordance with this aspect of the invention, the pH and molarity of an aqueous solution of toxin A are adjusted to precipitate toxin A, without precipitating the remaining proteins, whereby pure toxin A, is recovered.

More particularly, the pH of the aqueous solution is adjusted to a pH of less than 6.0 and at which toxin A precipitates without precipitation of other proteins or denaturation of the toxin, and the molarity of the aqueous solution is adjusted to less than 0.1M and at which toxin A precipitates without precipitation of other proteins. In general the pH is at least 5.0, with the pH preferably being from 5.3 to 5.7, with the best results being achieved at pH 5.5. The molarity of the solution is generally at least 0.001 M, with best results being achieved at 0.01M.

The molarity and pH may be achieved by using a suitable salt buffer; e.g., a sodium acetate buffer. The adjustment of molarity may be conveniently achieved by dialysis, although other procedures are applicable.

The precipitated pure toxin A is recovered from the aqueous solution and may be soublized in water at a buffered pH of about 7.5.

The partially purified toxin A, which is purified in accordance with the invention to produce pure toxin A may be recovered by procedures generally known in the art. For example, the supernatent from a cell culture of a toxigenic C. difficile strain is concentrated with an ultrafiltration membrane that retains only large molecules (over 100,000 M.W.) and the retained material is applied to a chromatographic column. The column (DEAE) is then eluted with gradients of sodium chloride (the first gradient is 0.05-0.25 M MaCl with a 0.3 M NaCl wash and the second gradient is 0.3-0.6 NaCl), with the first gradient eluting toxin A and the second gradient toxin B.

The term "pure toxin A" as used herein, indicates that the toxin A preparation is free of contaminating substances (only toxin A is present) when examined by a variety of highly resolving techniques known in the art. The term partially purified, as used herein, indicates that some contaminants, but not all, have been removed.

Pure toxin A when prepared by the procedures described above is pure by the criteria of: a single band on acrylamide gel electrophoresis when done with 100 ug of protein per gel rod (Davis, SDS, and gradient gels); a single immunoprecipitin arc on crossed immunoelectrophoresis plates with antisera made to the complex mixture of *C. difficile* antigens; and pure toxin A when injected into animals elicits production of a mono-specific antibody to toxin A.

The mono-specific antibody for toxin A of *C. difficile* and the mono-specific antibody for toxin B of *C. difficile* may be prepared by several different procedures.

In accordance with one procedure, *C. difficile* culture supernatant fluids produced by a known cultivating procedure are boiled to destroy all heat-labile protein antigens (toxin and non-toxin antigen) and thereby provide material containing only the heat-stable antigens of *C. difficile*. These antigens are then supported on a first cyanogen bromide activated Sepharose column.

Partially purified toxin A and partially purified toxin B, each obtained by elution from a DEAE chromatographic column, as hereinabove described, are coupled to a second and third cyanogen bromide activated Sepharose column, respectively.

Antibodies to crude *C. difficile* antigens toxin (such toxin includes both toxin A and toxin B as well as many other antigens produced by the bacterium) are produced in a suitable animal; e.g. goats, and the elicited antibody is comprised of an antibody mixture to *C. difficile* antigens (such antibody mixture includes antibodies for toxin A and toxin B, as well as antibodies to the non-toxin antigens, including antibodies to the heat-stable antigens.) The non-toxin antibodies (except the antibodies to the non-toxin heat-stable antigens) are removed from the antibody mixture by contact with whole cells of a non-toxic strain of *C. difficile* to thereby bind the antibodies to nontoxins except for the antibodies to the nontoxic heat-stable antigens.

Subsequently, the antibody mixture (which now contains the antibodies for the toxins, and the antibodies to the non-toxic heat-stable antigens) is then applied to the first column on which the heat-stable antigens of *C. difficile* are supported, whereby the sugar antibodies to the heat-stable antigens become bound.

The mixture which is free of antibody against the heat-stable antigens and contains antibodies to toxins A and B is then divided into two parts, with one part being applied to the second column on which pure toxin A is supported, and the other part being applied to the third column on which partially purified toxin B is supported, whereby in the second column, the antibody to toxin A becomes selectively bound to the supported toxin A and in the third column, the antibody to toxin B becomes selectively bound to the supported toxin B.

The antibodies for toxin A and the antibodies for toxin B are each subsequently eluted from the second and third columns, respectively; e.g., by the use of potassium thiocyanate to thereby, respectively, produce mono-specific antibody for toxin A and mono-specific antibody for toxin B.

In some cases as hereinafter described, the mixture of antibody for toxin A and antibody for toxin B (after removal of non-toxic antigens) may be used without separation into mono-specific antibody for each of the toxins, e.g., in an assay for toxigenic *C. difficile*.

Alternatively, mono-specific antibody to toxin A may be produced by applying the crude *C. difficile* antibody onto a column support with immobilized pure toxin A. The non-toxin A antibodies are removed from the column by extensive washing and the remaining antibodies, which are attached to the toxin A, are eluted with potassium thiocyanate.

Alternatively, mono-specific antibody to toxin A may be produced from purified toxin A, prepared as hereinabove described, by injecting toxin A (mixed with some formaldahyde to decrease toxicity without destroying antigenicity or neutralized with antibody) into a suitable animal; e.g. a goat. The mono-specific antibody to toxin A is then recovered by the procedure described in the preceding paragraph.

The mono-specific antibodies and the toxins of the present invention may be supported on a solid support for use in an assay for *C. difficile*. Alternatively, such antibodies and toxins may be used in such an assay in an unsupported form.

In using a solid support, the solid support may be any of a wide variety of solids, and may be employed in any one of a wide variety of forms; e.g. plates, trays, particles, tubes, sheets, etc.

As representative examples of suitable supports, there may be mentioned: synthetic polymer supports, such as polystyrene, polypropylene, substituted polystyrene (e.g. aminated or carboxylated polystyrene), polyacrylamides, polyamides, polyvinylchloride, etc.; glass beads, agarose; etc. The supports may include reactive groups, e.g. carboxyl groups, amino groups, etc. to permit direct linking to the support.

The antibodies and toxins of the present invention may be supported on a solid support in a variety of ways; for example, by adsorption, covalent coupling, activation of a suitable support, with protein A, etc.

As representative examples of suitable coupling agents there may be mentioned: dialdehydes; for example glutaraldehyde, succinaldehyde, malonaldehyde, etc; unsaturated aldehyde, e.g., acrolein, methacrolein, crotonaldehyde, etc.; carbodiimides, diisocyanates; dimethyladipimate; cyanuric chloride etc. The selection of a suitable coupling agent should be apparent to those skilled in the art from the teachings herein.

Similarly, the antigen may be supported by activation of a suitable support; for example, cyanogen bromide activated agarose.

In accordance with an aspect of the present invention, the antibodies and toxins of the present invention may be used in an assay for either toxin A, or toxin B of *C. difficile* or for toxigenic *C. difficile* (both toxin A and toxin B).

In some of such assays, one or more of such substances are used in a "labelled" or "tagged" form, and such labels or tags are of a type known in the art for use in assays. Thus, for example, the label or tag may be a radioactive substance, such as radioactive iodine, radioactive cobalt, tritium, etc.; an enzyme; a fluorescent material; a chemiluminescent material, etc.

The label may be added to the various substances by procedures as generally practiced in the art. Similarly, the label or tag may be detected by procedures known in the art; for example, counters for radioactive labels, colorimetric detection of enzymes, etc.

The antibodies and toxins of the present invention may be used in supported and/or unsupported form for the assay of *C. difficile*.

In accordance with one embodiment of the invention, there is provided an assay for toxin A of *C. difficile* by use of the mono-specific antibody for toxin A.

In accordance with one aspect of this embodiment, antibody to *C. difficile* is supported on a solid support; for example, a microtiter plate. The supported *C. difficile* antibody is then contacted with a sample to be analyzed (analyte) such as a dilution of patient feces, and as a result of such contact, any toxin A present in the analyte, as well as other antigens of *C. difficile,* become bound to the supported *C. difficile* antibody. Subsequently, the bound analyte portion is contacted with monospecific antibody for toxin A of *C. difficile,* (raised in an animal different than the animal in which *C. difficile* antibody was raised,) and such mono-specific antibody is only bound by any toxin A present in the bound analyte portion.

This mono-specific antibody may itself be labelled with an enzyme, flourescent material, or radioactive material as described previously, and the presence of toxin A can be determined by detecting the presence of this label. Alternatively, the monospecific antibody bound to toxin A can be detected by use of labelled antibody specific for antibody of the animal in which the mono-specific antibody was raised; this binds to the mono-specific antibody attached to toxin A. This method is referred to in the art as a double antibody sandwich form of the ELISA assay.

The presence of toxin A in the analyte may be determined by its interaction with mono-specific toxin A antibody in the assay.

The above procedure may also be employed for the determination of toxin B in an analyte by use of mono-specific antibody for toxin B in place of mono-specific antibody for toxin A.

In another assay for toxin A of *C. difficile,* monospecific antibody for toxin A may be supported on a solid support; for example, a microtiter plate, and the supported mono-specific antibody for toxin A is contacted with analyte suspected of containing toxin A, whereby any toxin A present in the sample (and only toxin A) becomes bound to the supported mono-specific antibody. The presence and/or amount of bound toxin A may then be determined by contacting the bound toxin A with *C. difficile* antibody, in labelled form, with such labelled antibody being bound by any bound toxin A. The presence and/or amount of toxin A present in the analyte is then determined by determining the presence and/or amount of the bound labelled antibody.

The above procedure may also be used in an assay for toxin B by substituting mono-specific antibody for toxin B for the mono-specific antibody for toxin A.

In accordance with a further assay for toxin A, the analyte containing or suspected of containing toxin A, is contacted with a solid support, such as a microtiter tray so that at least the toxin A in the analyte is supported on the solid support. The presence of this toxin A is then detected by mono-specific antibody for toxin A. The supported toxin A selectively binds only the mono-specific antibody for toxin A. Thus, the mono-specific antibody is supported on a solid support through the supported toxin A of the analyte. This antibody can have a label, such as an enzyme attached, that will allow its detection or a labelled antibody can be used that reacts with the antibody bound to the toxin A (sandwich ELISA method). The presence and/or amount of bound labelled antibody is a measure of the presence or amount of toxin A in the analyte.

In accordance with a still further assay, toxin A may be detected by an agglutination procedure. According to such procedure, solid particles sensitized with mono-specific antibody to toxin A are contacted with analyte containing or suspected of containing toxin A with the presence of toxin A causing agglutination of such particles.

The agglutination assay is also suitable for detecting toxin B by using monospecific antibodies to toxin B in place of the mono-specific to toxin A.

In accordance with still another assay, toxin A may be determined by an inhibition of agglutination procedure by contacting solid particles sensitized with purified toxin A (or sensitized with crude *C. difficle* toxin, which includes toxin A) with both analyte containing or suspected containing toxin A, and mono-specific antibody for toxin A of *C. difficile,* with the presence of toxin A in the analyte inhibiting agglutination of the sensitized particles by the mono-specific antibody. Such procedure may also be employed for determining toxin B by sensitizing the particles with crude toxin and use of mono-specific antibody for toxin B.

As a further modification, the assay can be directed to determining toxigenic *C. difficile* (toxin A and/or toxin B) by use of antibody for toxigenic *C. difficile* (a mixture of the mono-specific antibody for toxin A and the mono-specific antibody for toxin B which is free of determinant sites for non-toxic antigens). By using a mixture of such mono-specific antibodies, it is possible to determine the presence of either toxin A or toxin B in a sample.

The present invention will be further described with respect to the following examples; however, the scope of the invention is not to be limited thereby:

EXAMPLE I

This example is directed to the production of mono-specific antibody for toxin A, and mono-specific antibodies for toxin B.

Bacteria and growth conditions.

Two-liter brain heart infusion dialysis tube flasks were inoculated with 0.1 ml of actively growing cultures of *C. difficile* VPI strain 11186 (non-toxigenic) and *C. difficile* VPI strain 10463 (toxigenic), and the flasks were incubated at 37° C. for 3 days. The cells were obtained from inside the dialysis sack by centrifugation of the contents (9,000 xg for 15 minutes).

Preparation of boiled cell wash (BCW)-Sepharose, Toxin A-(ToxA)-Sepharose, and Toxin B (ToxB)-Sepharose.

Strain 10463 packed cells (ca. 15 ml obtained from 12 flasks) were washed 3 times (30 ml per wash) with 0.1 M $NaHCO_3$ -0.5M NaCl, pH 8. Cell washes were pooled and the pool was heated at 100° C. for 15 minutes. The precipitated material was removed by centriguation (12,000×g for 30 minutes) and the supernatant fluid (ca. 34 mg. of protein in 90 ml) was added to 60 ml of Sepharose 4B (Pharmacia Fine Chemicals, Uppsala, Sweden) which had been activiated with 18 g of CNBr. The suspension was gently mixed at 4° C. overnight and uncoupled material was removed by washing the gel with one bed volume of 0.1 M $NaHCO_3$-0.5M NaCl. Protein analysis of the wash indicated that the gel prepartion contained ca. 0.3 mg of protein per ml gel. The remaining active groups on the Sepharose gel were blocked by adding one bed volume of 1 M ethanolamine, pH 8, and mixing the gel at 4° C. overnight. The gel, designated BCW-Sepharose, was washed 4X with alternating volumes (2 bed volumes per wash) of 0.1 M sodium acetate-0.5 M NaCl, pH 4, and 0.1 M $NaHCO_3$-0.5 M NaCl, pH 8.

Partially purified toxin A and toxin B were prepared by ion exchange chromatography on DEAE Sepharose CL-6B (Pharamcia Fine Chemicals) as described in Example II and each preparation was dialyzed overnight at 4° C. against 0.1 M NaHCO$_3$-0.5 M NaCl. Toxin A (ca. 3.3 mg of protein in 20 ml) and toxin B (ca. 1.1 mg of protein in 20 ml) were each coupled, as described for BCW-Sepharose, to 20 ml of Sepharose 4B which has been activiated with 7 g of CNBr. Protein analyses of the washes indicated that ToxA-Sepharose and ToxB-Sepharose contained 170 ug of protein and 54 ug of protein per ml of gel, respectively.

Purification of monospecific antisera against Toxins A and B.

Goat antiserum was prepared, as previously described, using refrigerated formaldehyde (Ehrich, M., R. L. Van Tassell, J. M. Libby, and T. D. Wilkins, 1980. Production of *Clostridium difficile* antitoxin. Infect. Immun. 28:1041–1043.) against a crude *C. difficile* toxin preparation containing Toxins A and B. Antiserum (5 ml) was added to a suspension of strain 11186 cells (1.5 ml packed cells in 3 ml 0.85% NaCl) and the mixture was gently homogenized with a Potter Elvehjam tissue grinder and then rotated for 2 h at room temperature. The cells were subsequently removed by centrifugation (12,000×g for 30 min) and the supernatant fluid was passed through a 0.45 um membrane and concentrated to 1X with a minicon-B15 concentrator (Amicon Corp, Lexington, Mass.). Strain 11186 cell-adsorbed antiserum (4.1 ml) was applied to a column (1.5 by 31.4 cm) of BCW-Sepharose, and nonadsorbed material was eluted at room temperature with 2 bed volumes of 0.1 M NaHCO$_3$-0.5 M NaCl, pH 8, at a flow rate of 40 ml/h. The eluate was concentrated to 1X by ultrafiltration in a stirred cell equipped with a PM 10 membrane (Amicon Corp.). The BCW-Sepharose-eluate (4.1 ml) was divided into 2 equal portions which were applied to columns (1 by 25 cm) of ToxA-Sepharose and ToxB-Sepharose. Nonadsorbed material was eluted at room temperature from each column with 2 bed volumes of 0.1 M NaHCO$_3$-0.5 M NaCl, pH 8, at a flow rate of 40 ml/h. Eluates were concentrated to 1X by ultrafiltration.

Elution of antibodies bound to ToxA-Sepharose and ToxB-Sepharose.

Following the elution of nonadsorbed material from ToxA-Sepharose and ToxB-Sepharose, the columns were washed with 0.1 M NaHCO$_3$-0.5 M NaCl., pH 8, until there was no measurable adsorbance at 280 nm. Antibodies bound to the gels were eluted by applying 5 ml of 3.5 M KSCN, pH 6.8, to each column and washing with 0.1 M NaHCO$_3$-0.5 M NaCl. Approximately 2 bed volumes were collected from each column. The eluates were dialyzed against 4 l of 0.1 M borate-buffered saline pH 8.5, at 4° C. overnight and concentrated to 1X by ultrafiltration.

The antibody eluted from the ToxA-Sepharose column is the mono-specific antibody for toxin A of *C. difficile* and the antibody eluted from the ToxB-Sepharose column is the mono-specific antibody for toxin B of *C. difficile.*

Purification of IgG fraction.

The eluted antibodies from the ToxA-Sepharose and ToxB-Sepharose column were purified by chromatography on DEAE Affi-Gel Blue (Bio-Rad Laboratories, Rockville Centre, NY) as recommended by the manufacturer for the purification of rabbit IgG. Antiserum samples (2 ml) were applied to a column of DEAE Affi-Gel Blue (1 by 31.8 cm) and eluted at a flow rate of 20 ml/h. Fractions (2 ml) containing purified IgG were pooled and concentrated to 1X by ultrafiltration.

EXAMPLE II

This example is directed to production of pure toxin A of *C. difficile.*

Bacterial strain.

*Clostridium difficile* VPI strain 10463 was grown in two liter brain heart infusion (BHI) dialysis flasks for 72 hours at 37° C. After centrifugation at 8000×g for 10 minutes and filtration through a 0.45 um membrance filter (Millipore Corp., Bedford, MA), the culture supernatant (c.750 ml) was concentrated to 50 ml by ultrafiltration, at 4° C., using an XM-100 membrane filter (Amicon Corp., Lexington, MA) with a thin channel type concentrator. The retentate was washed with 1500 ml of 50 mM TRIS-HCl buffer, pH 7.5 (4° C.) and concentrated to a final volume of 40–50 ml. This removed many small molecular weight contaminants. The concentrated supernatant was loaded onto a 2.5 by 10 cm DEAE Sepharose CL-6B column which has been equilibrated with 50 mM TRIS-HCl, pH 7.5. After sample loading, the column was washed with 200 ml of 50 mM TRIS-HCl, pH 7.5, containing 0.05 M NaCl. The sample was eluted first with a 300 ml linear NaCl gradient in 50 mM TRIS-HCl buffer (0.05–0.25 M NaCl), followed by 150 ml of 50 mM TRIS-HCl, pH 7.5, containing 0.3 M NaCl. A second 300 ml linear gradient (0.3–0.6 M NaCl) in the same buffer followed the 0.3 M NaCl wash. The flow rate of the columns was 55–60 ml per hr (Gravity) at 4° C. Fractions (4.2 ml) were collected and assayed for cytotoxicity using CHO-Kl cells.

The fractions containing the highest cytotoxic titers were pooled, filter-sterilized and stored at 4° C. The toxins that eluted in the first and second NaCl gradients were designated Toxins A and B respectively, and are partially purified toxins A and B, respectively.

Five to ten ml of the toxic fractions from the first DEAE gradient (Toxin A) were dialyzed against one liter of 0.01 M sodium acetate buffer pH 5.5 at 4° C. for 18–24 hours. The dialysate was centrifuged to recover the precipitate at 169×g for 10 minutes and was then washed with 5 ml of the same acetate buffer and centrifuged again. The precipitate was solubilized in 5–10 ml of 50 mM TRIS-HCl, pH 7.5 containing 0.05 M NaCl and the solution of purified toxin A was filter-sterilized and stored at 4° C.

EXAMPLE III

The following buffers are used in an assay for Toxins A and B.

Carbonate buffer (coating buffer)
1.59 g Na$_2$CO$_3$
2.93 g NaHCO$_3$
0.20 g NaN$_3$
bring to 1 liter with dH$_2$O; pH 9.6;
store at room temperature (use within 2 weeks)
Phosphate-buffered saline-Tween 20 (PBS-T)
8.0 g NaCl
0.2 g KH$_2$PO$_4$
2.9 g Na$_2$HOP$_4$.12H$_2$O (2.2 g Na$_2$HOP$_4$.7H$_2$O)
0.2 g KCl
0.5 ml Tween 20 (polyoxyethylene sorbitan monolaurate)
0.2 g NaN$_3$
bring to liter with dH$_2$O; pH 7.4;

Diethanolamine buffer (for alkaline phosphatase substrate)

97 ml diethanolamine
800 ml dH$_2$O
0.2 g NaN$_3$
100 mg MgCl$_2$.6H$_2$O
titrate to pH 9.8 with 1 M HCl and bring volume to 1 liter with dH$_2$O; store in dark bottle at room temperature; for substrate solution, add 1 mg substrate per ml buffer;

Assay for *Clostridium difficile* Toxins A and B (1) Add 200 ul of 1/10,000 dilution (in carbonate buffer, pH 9.6) of rabbit antiserum (antibody to *C. difficile*) to each well of a Dynatech Immulon type 2 microtiter plate. Incubate at 4° C. overnight.

(2) Empty plate and add 200 ul of PBS-T containing 0.5% bovine serum albumin to each well. Incubate plate at 37° C. for 30 minutes.

(3) Empty plate and add 200 ul of PBS-T to each well. Incubate plate at room temperature for 5 minutes.

(4) Empty plate and add 200 ul of sample dilution or toxin dilution (1:2) in PBS-T to wells. Incubate plate either at 37° C. for 1 hour or at room temperature overnight.

(5) Empty plate and wash each well 3 times with PBS-T.

(6) Add 200 ul of 1/1,000 dilution in PBS-T of monospecific antibody for either Toxin A or Toxin B to each well. Incubate plate at 37° C. for 1 hour.

(7) Empty plate and wash each well 3 times with PBS-T.

(8) Add 200 ul of 1/800 dilution (in PBS-T) of rabbit antigoat IgG coupled to alkaline phosphatase to each well. Incubate plate at 37° C. for 1 hour.

(9) Empty plate and wash each well 3 times with PBS-T.

(10) Add 200 ul of p-nitrophenylphosphate (1 mg/ml in diethanolamine buffer) to each well. Incubate plate at room temperature for 1 hour.

(11) Add 20 ul of 5 N NaOH to each well to terminate the reaction.

(12) Mix contents of each well with 0.8 ml dH$_2$O (total volume of assay mixture ca. 1 ml) and measure the absorbance at 405 nm.

The present invention is particularly advantageous in that it is possible to produce antibodies which are specific for only the toxins of *C. difficile*. As a result, there is provided an assay which is directed to determining the presence of these toxins, rather than *C. difficile*, which will reduce or eliminate false positives.

Furthermore, the present invention offers the advantage of permitting an assay which can be directed to either of the toxins or both toxins.

An assay for the toxins in accordance with the invention is rapid and also less costly than prior assays.

Numerous modifications and variations of the present invention are possible in light of the above teachings, and, therefore, within the scope of the apppended claims, the invention may be practiced otherwise than as specifically described.

What is claimed is:

1. In an assay process for toxin A of *C. difficile* wherein an analyte containing toxin A is contacted with an antibody, the improvement comprising:
contacting said analyte with monospecific antibody for toxin A of *C. difficile* to bind only toxin A to said mono-specific antibody.

2. The process of claim 1 wherein in the assay antibody to *C. difficile* is supported on a solid support, the supported *C. difficile* antibody is contacted with analyte to bind *C. difficile* antigen to the supported *C. difficile* antibody and subsequently the bound antigen is contacted with mono-specific antibody in a labelled form and the presence of said toxin is determined by detecting the presence of bound label.

3. The process of claim 2 wherein the label is an enzyme label.

4. The process of claim 3 wherein the enxyme label is alkaline phosphatase.

5. The process of claim 1 wherein in the assay antibody to *C. difficile* is supported on a solid support, the supported *C. difficile* antibody is contacted with analyte to bind the *C. difficile* antigen to the *C. difficile* antibody, the antigen is contacted with mono-specific antibody to bind mono-specific antibody to toxin A of the bound antigen, subsequently bound mono-specific antibody is contacted with a labelled form of antibody for the mono-specific antibody, and the presence of said toxin A is determined by detecting the presence of bound label.

6. The process of claim 5 wherein the label is an enzyme label.

7. The process of claim 6 wherein the enzyme label is alkaline phosphatase.

8. The process of claim 1 wherein the monospecific antibody is supported on solid particles, and the presence of toxin A is determined by agglutination of the solid particles.

9. The process of claim 1 wherein the antibody is supported on a solid support.

10. The process of claim 9 wherein the analyte is present in a feces sample.

11. In an assay process for toxin B of *C. difficile* wherein an analyte containing toxin B is contacted with an antibody, the improvement comprising:
contacting said analyte with monospecific antibody for toxin B of *C. difficile* to bind only toxin B to said mono-specific antibody.

12. The process of claim 11 wherein in the assay antibody to *C. difficile* is supported on a solid support, the supported *C. difficile* antibody is contacted with analyte to bind *C. difficile* antigen to the supported *C. difficile* antibody and subsequently the bound antigen is contacted with mono-specific antibody in a labeled form and the presence of said toxin is determined by detecting the presence of bound label.

13. The process of claim 12 wherein the label is an enzyme label.

14. The process of claim 13 wherein the enzyme label is alkaline phosphatase.

15. The process of claim 11 wherein in the assay antibody to *C. difficile* is supported on a solid support, the supported *C. difficile* antibody is contacted with analyte to bind the *C. difficile* antigen to the *C. difficile* antibody, the antigen is contacted with mono-specific antibody to bind mono-specific antibody to toxin B of the bound antigen, subsequently bound mono-specific antibody is contacted with a labelled form of antibody for the mono-specific antibody, and the presence of said toxin B is determined by detecting the presence of bound label.

16. The process of claim 15 wherein the label is an enzyme label.

17. The process of claim 16 wherein the enzyme label is alkaline phosphatase.

18. The process of claim 11 wherein the monospecific antibody is supported on solid particles and the presence of toxin B is determined by agglutination of the solid particles.

19. The process of claim 11 wherein the antibody is supported on a solid support.

20. The process of claim 19 wherein the analyte is present in a feces sample.

21. In an assay process for toxigenic *C. difficile* wherein an analyte containing toxigenic *C. difficile* is contacted with an antibody, the improvement comprising:

contacting said analyte with antibody specific for toxins of *C. difficile* to bind only *C. difficile* toxins to the antibody.

22. The process of claim 21 wherein in the assay antibody to *C. difficle* is supported on a solid support, the supported *C. difficile* antibody is contacted with analyte to bind *C. difficile* antigen to the supported *C. difficile* antibody and subsequently the bound antigen is contacted with mono-specific antibody in a labelled form and the presence of said toxin is determined by detecting the presence of bound label.

23. The process of claim 2 wherein the label is an enzyme label.

24. The process of claim 23 wherein the enzyme label is alkaline phosphatase.

25. The process of claim 21 wherein in the assay antibody to *C. difficile* is supported on a solid support, the supported *C. difficile* antibody is contacted with analyte to bind the *C. difficile* antigen to the *C. difficile* antibody, the antigen is contacted with mono-specific antibody to bind mono-specific antibody to *C. difficile* toxins of the bound antigen, subsequently bound mono-specific antibody is contacted with a labelled form of antibody for the mono-specific antibody, and the presence of said *C. difficile* toxins is determined by detecting the presence of bound label.

26. The process of claim 25 wherein the label is an enzyme label.

27. The process of claim 26 wherein the enzyme label is alkaline phosphatase.

28. The process of claim 21 wherein the antibody is supported on solid particles and the presence of toxigenic *C. difficile* is determined by agglutination of the solid particles.

29. A process for providing antibodies specific for toxins of *C. difficile*, comprising:

contacting *C. difficile* antibody, which includes antibodies specific for toxins of *C. difficile*, antibody to non-toxic protein antigen and antibody to non-toxic heat stable antigen with non-toxic *C. difficile* protein antigen to bind antibody to non-toxic protein antigen thereto;

contacting said *C. difficile* antibody free of antibody to non-toxic protein antigen with a non-toxic heat stable antigen of *C. difficile* to bind the antibody for the non-toxic heat stable antigen thereto; and recovering antibody specific for toxins of *C. difficile*.

30. The process of claim 29 wherein the non-toxic *C. difficile* protein antigen is in the form of whole cells of a non-toxic strain of *C. difficile*.

31. The process of claim 30 wherein the non-toxic heat stable antigen of *C. difficile* is supported on a solid support.

32. The process of claim 29 wherein the antibody is supported on a solid support.

33. A process for providing mono-specific antibody for toxin A of *C. difficile*, comprising:

contacting *C. difficile* antibody, which includes antibodies specific for toxins of *C. difficile*, antibody to non-toxic protein antigen and antibody to non-toxic heat stable antigen with non-toxic *C. difficile* protein antigen to bind antibody to non-toxic protein antigen thereto;

contacting said *C. difficile* antibody free of antibody to non-toxic protein antigen with a non-toxic heat stable antigen of *C. difficile* to bind the antibody for the non-toxic heat stable antigen thereto;

recovering antibody specific for toxins of *C. difficile*;

contacting antibody specific for toxins of *C. difficile* with toxin A of *C. difficile* supported on a solid support to bind mono-specific antibody for toxin A thereto; and subsequently eluting mono-specific antibody for toxin A therefrom.

34. The process of claim 33 wherein the non-toxic *C. difficile* protein antigen is in the form of whole cells of a non-toxic strain of *C. difficille*.

35. The process of claim 34 wherein the non-toxic heat stable antigen of *C. difficile* is supported on a solid support.

36. A process for providing mono-specific antibody for toxin B of *C. difficile*, comprising:

contacting *C. difficile* antibody, which includes antibodies specific for toxins of *C. difficile*, antibody to non-toxic protein antigen and antibody to non-toxic heat stable antigen with non-toxic *C. difficile* protein antigen to bind antibody to non-toxic protein antigen thereto;

contacting said *C. difficile* antibody free of antibody to non-toxic protein antigen with a non-toxic heat stable antigen of *C. difficile* to bind the antibody for the nontoxic heat stable antigen thereto;

recovering antibody specific for toxins of *C. difficile*;

contacting antibody specific for toxins of *C. difficile* with toxin B of *C. difficile* supported on a solid support to bind mono-specific antibody for toxin B thereto; and subsequently eluting mono-specific antibody for toxin B therefrom.

37. The process of claim 36 wherein the non-toxic *C. difficile* protein antigen is in the form of whole cells of a non-toxic strain of *C. difficile*.

38. The process of claim 37 wherein the non-toxic heat stable antigen of *C. difficile* is supported on a solid support.

* * * * *